United States Patent
Empfield et al.

[11] Patent Number: 5,900,432
[45] Date of Patent: * May 4, 1999

[54] THERAPEUTIC N-(4-BENZOYL-2-METHYL-PHENYL)-3,3,3-TRIFLUORO-2-HYDROXY-2-METHYL-PROPANAMIDES

[75] Inventors: James Roy Empfield, Bear; Cyrus John Ohnmacht, Wilmington; Keith Russell, Newark; Diane Amy Trainor; Paul James Warwick, Jr., both of Wilmington, all of Del.

[73] Assignee: Zeneca Limited, United Kingdom

[*] Notice: This patent is subject to a terminal disclaimer.

[21] Appl. No.: 08/542,114

[22] Filed: Oct. 12, 1995

Related U.S. Application Data

[63] Continuation of application No. 08/212,460, Mar. 11, 1994, Pat. No. 5,482,969.

[30] Foreign Application Priority Data

Mar. 15, 1993 [GB] United Kingdom ............. 9305295

[51] Int. Cl.$^6$ .................. A61K 31/16; C07C 237/20; C07C 51/255; C07C 233/01
[52] U.S. Cl. .................. 514/522; 514/613; 558/415; 564/158; 564/171; 564/174
[58] Field of Search .................. 514/522, 613; 558/415; 564/158, 171, 174

[56] References Cited

U.S. PATENT DOCUMENTS

| | | | |
|---|---|---|---|
| 3,291,837 | 12/1966 | Goldberg et al. | 568/333 |
| 3,365,485 | 1/1968 | Bell | 560/250 |
| 3,468,878 | 9/1969 | Bell | 564/49 |
| 3,715,375 | 2/1973 | Shen et al. | 568/49 |
| 3,998,890 | 12/1976 | Karrer et al. | 514/522 |
| 4,191,775 | 3/1980 | Glen | 514/522 |
| 4,239,776 | 12/1980 | Glen | 514/522 |
| 4,282,218 | 8/1981 | Glen et al. | 514/178 |
| 4,386,080 | 5/1983 | Crossley et al. | 514/522 |
| 4,535,092 | 8/1985 | Hughes | 514/438 |
| 4,636,505 | 1/1987 | Tucker | 514/256 |
| 4,845,119 | 7/1989 | Hughes et al. | 514/450 |
| 4,873,329 | 10/1989 | Hughes et al. | 544/265 |
| 4,880,839 | 11/1989 | Tucker | 514/613 |
| 5,032,592 | 7/1991 | Hughes et al. | 514/256 |
| 5,272,163 | 12/1993 | Russell et al. | 514/347 |
| 5,482,969 | 1/1996 | Empfield et al. | 514/522 |

FOREIGN PATENT DOCUMENTS

| | | |
|---|---|---|
| 2 020 971 | 1/1991 | Canada . |
| 0 181 568 | 5/1986 | European Pat. Off. . |
| 0 189 142 | 7/1986 | European Pat. Off. . |
| 0 253 503 | 1/1988 | European Pat. Off. . |
| 0 274 867 | 7/1988 | European Pat. Off. . |
| 0 409 413 | 1/1991 | European Pat. Off. . |
| 0 409 414 | 1/1991 | European Pat. Off. . |
| 0 524 781 | 1/1993 | European Pat. Off. . |
| 7008627-Q | 6/1969 | Netherlands . |
| 7008629-Q | 6/1969 | Netherlands . |
| WO 93/23358 | 11/1993 | WIPO . |

OTHER PUBLICATIONS

R Bayles et al., "The Smiles rearrangement of 2–aryloxy–2–methylpropanamides. Synthesis of N–aryl–2–hydroxy–2–methylpropanamides" *Synthesis*, (1977), 31–33.

G Edwards et al., "Structure–activity relationships of potassium channel openers", *Trends in Pharmacological Sciences*, (1990), 11, 417–422.

B. Delfort, et al. "Ethynyl–Terminated Polyethers from New End–Capping Agents: Synthesis and Characterization" *Journal of Polymer Science: Part A: Polymer Chemistry*, (1990), 28 (9), 2451–64.

J.J. Morris, et al. "Non–Steroidal Antiandrogens. Design of Novel Compounds Based on Antiandrogens" *J. Med. Chem.*, (1991), 34, 447–455.

R. C. Small et al. "Potassium Channel Opening Drugs and the Airways", *Brazilian J Med Biol Res*, (1992) 25, 983–998.

*Primary Examiner*—Alan L. Rotman
*Attorney, Agent, or Firm*—Liza D. Hohenschutz; Richard A. Elder

[57] ABSTRACT

Compounds of formula I:

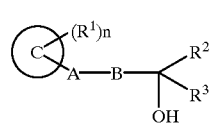

wherein, ring C, A—B, $R^1$, n, $R^2$, and $R^3$ have any of the meanings given in the specification, and their pharmaceutically acceptable salts are useful in the treatment of urinery incontinence. Also disclosed are pharmaceutical compositions, processes for preparing the compounds of formula I and intermediates.

7 Claims, No Drawings

THERAPEUTIC N-(4-BENZOYL-2-METHYL-PHENYL)-3,3,3-TRIFLUORO-2-HYDROXY-2-METHYL-PROPANAMIDES

This is a continuation application of application Ser. No. 08/212,460 filed on Mar. 11, 1994, now U.S. Pat. No. 5,482,969.

This invention relates to a novel group of compounds which are useful in the treatment of bladder instability in mammals such as man. More specifically, this invention relates to this group of compounds, their use in the treatment of urinary incontinence in mammals (including man), processes for preparing them and pharmaceutical compositions containing them.

It is known that bladder tissue is excitable and that urinary incontinence can be caused by uncontrolled or unstable bladder contractions. A group of compounds have been found that are unexpectedly capable of relaxing bladder smooth muscle, thus preventing or ameliorating uncontrolled or unstable bladder contractions. Hence, the compounds may be useful for the treatment of urge incontinence, which includes for example detrusor instability, which may result from cystitis, urethritis, tumors, stones, diverticuli or outflow obstruction; and detrusor hyperreflexia, which may result from stroke, dementia, Parkinsons, suprasacral spinalcord injury or suprasacral spinalcord disease.

This invention provides a compound of formula I (formula set out, together with other formulae referred to by Roman numerals, on pages following the Examples), wherein:

Ring C is phenyl or carbon-linked heteroaryl selected from pyridyl, pyrazinyl, pyrimidinyl and pyridazinyl; wherein said phenyl or heteroaryl is substituted on carbon at one or both positions meta to the position of A—B attachment or on carbon at the position para to the position of A—B attachment by a group selected from cyano, trifluoromethyl, nitro, trifluoromethoxy, trifluoromethylthio and a group ArY; and further, wherein said phenyl or heteroaryl is substituted on carbon at any remaining meta position(s) or para position by a group or groups independently selected from hydrogen, (1–4C)alkyl, (1–4C)haloalkyl, (1–4C)alkoxy, (1–4C)haloalkoxy, (1–4C)alkenyloxy, cyano, nitro, halo, hydroxy and trifluoromethylthio; in which Ar is selected from the group consisting of;
  phenyl, a carbon-linked six-membered heteroaryl ring containing 1–2 nitrogens atoms and a carbon-linked five-membered heteroaryl ring containing from 1–2 heteroatoms selected from nitrogen, oxygen, and sulfur; wherein said phenyl or heteroaryl ring Ar may be substituted at carbon, with 0–4 substituents selected from (1–4C)alkyl, (1–4C)haloalkyl, (1–4C)alkoxy, (1–4C)haloalkoxy, (2–4C)alkenyloxy, cyano, nitro, halo and trifluoromethylthio;
  Y is selected from carbonyl, sulfinyl and sulfonyl;
A–B is selected from NHCO, OCH$_2$, SCH$_2$, NHCH$_2$, trans-vinylene, and ethynylene;
$R^1$ is linked to Ring C at a carbon ortho to the position of A–B attachment and is selected from the group consisting of (1–4C)alkyl, (1–4C)haloalkyl, (1–4C)alkoxy, (1–4C)haloalkoxy, (2–4C)alkenyloxy, cyano, nitro, halo, trifluoromethylthio or hydroxy;
n is 1 or 2;
$R^2$ and $R^3$ are independently (1–3C)alkyl substituted by from 0 to 2k+1 atoms selected from fluoro and chloro wherein k is the number of carbon atoms in the said (1–3C)alkyl, provided that $R^2$ and $R^3$ are not both methyl; or $R^2$ and $R^3$, together with the carbon atom to which they are attached, form a 3–5 membered cycloalkyl ring optionally substituted by from 0 to 2m–2 fluorine atoms wherein m is the number of carbon atoms in said ring;
or a pharmaceutically acceptable in vivo hydrolyzable ester of said compound of formula I;
or a pharmaceutically acceptable salt of said compound or said ester; provided said compound is not N-(4-Benzoyl-2,6-dimethylphenyl)-3,3,3-trifluoro-2-hydroxy-2-methylpropanamide.

The invention further provides a method for the treatment of urinary incontinence, comprising administering to a mammal (including man) in need of such treatment an effective amount of a compound of formula I as defined above, or a pharmaceutically acceptable in vivo hydrolyzable ester of said compound of formula I or a pharmaceutically acceptable salt of said compound or said ester.

The invention further provides a pharmaceutical composition comprising a compound of formula I as defined above, or a pharmaceutically acceptable in vivo hydrolyzable ester of said compound of formula I or a pharmaceutically acceptable salt of said compound or said ester, and a pharmaceutically acceptable diluent or carrier.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo" is inclusive of fluoro, chloro, bromo, and iodo unless noted otherwise.

It will be appreciated by those skilled in the art that certain compounds of formula I contain an asymmetrically substituted carbon and/or sulfur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of urinary incontinence, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of urinary incontinence by the standard tests described hereinafter.

A particular value for Ring C is phenyl.
Particular values of Y include carbonyl and sulfonyl.
A particular value of Ar is phenyl.
Particular values of Ar as a carbon-linked six-membered heteroaryl ring containing 1–2 nitrogen atoms include 2-, 3-, and 4-pyridyl, 2-pyrazinyl, 2- and 4-pyrimidinyl, and 3- and 4-pyridazinyl.
Particular values of Ar as a carbon-linked five-membered heteroaryl ring containing from 1–2 heteroatoms selected from nitrogen, oxygen, and sulfur include 3-, 4- and 5-isothiazolyl, 2-, 4- and 5-oxazolyl, 2-, 4- and 5-thiazolyl, 2- and 3-furyl, and 2- and 3-thienyl.
A particular value for A—B is NHCO, OCH$_2$, SCH$_2$, NHCH$_2$, trans-vinylene or ethynylene.
Particular values of $R^1$ include for halo, fluoro and chloro; for (1–4C)alkyl, methyl and ethyl; for (1–4C)alkoxy, methoxy and ethoxy.
Particular values of $R^2$ and $R^3$ include (1–3C)alkyl substituted by from 0 to 2k+1 fluorine atoms, wherein k is the number of carbon atoms in said (1–3C)alkyl;

A more particular value for Y is carbonyl or sulfonyl.

More particular values of Ar as a six-membered heteroaryl ring containing 1–2 nitrogen atoms include 2,3-, and 4-pyridyl, and 2- and 4-pyrimidinyl.

More particular values of Ar as a five-membered heteroaryl ring containing from 1–2 heteroatoms include 3- and 4-isothiazolyl, 2- and 4-oxazolyl, 2- and 4-thiazolyl, 2- and 3-furyl, and 2- and 3-thienyl.

More particular values of $R^2$ include fluoromethyl, difluoromethyl, trifluoromethyl, 2,2,2-trifluoroethyl, and perfluoroethyl.

More particular values of $R^3$ include methyl, fluoromethyl, difluoromethyl, trifluoromethyl, 2,2,2-trifluoroethyl, and perfluoroethyl.

Particular compounds of formula I are compounds of formula Ia in which one of D and E is ArY and the other of D and E is selected from hydrogen, halo, cyano, methoxy, hydroxy and methyl; and wherein $R^1$, $R^2$, $R^3$, Ar and Y have the values defined above.

Particular compounds of formula I are compounds of formula Ib in which one of $R^9$ and $R^{10}$ is selected from the group consisting of (1–4C)alkyl, (1–4C)haloalkyl, (1–4C)alkoxy, (1–4C)haloalkoxy, (2–4C)alkenyloxy, cyano, nitro, halo and trifluoromethylthio; and the other of $R^9$ and $R^{10}$ is selected from the group consisting of hydrogen, (1–4C)alkyl, (1–4C)haloalkyl, (1–4C)alkoxy, (1–4C)haloalkoxy, (2–4C)alkenyloxy, cyano, nitro, halo and trifluoromethylthio; and in which $R^{11}$ is hydrogen, halo, cyano, methoxy, hydroxy or methyl; and wherein $R^2$, $R^3$, Ar and Y have the values defined above.

Particular compounds of formula I are those in which n is 1.

Particular compounds of formula I are those in which A—B is NHCO.

Particular compounds of formula I are those in which A—B is OCH$_2$, SCH$_2$, NHCH$_2$, trans-vinylene, and ethynylene.

More particular compounds of formula I are those in which A—B is OCH$_2$, trans-vinylene, and ethynylene.

A particular compound is N-(4-benzoyl-2-methyl)phenyl-3,3,3-trifluoro-2-hydroxy-2-methylpropanamide, N-(4-benzoyl-2-fluoro)phenyl-3,3,3-trifluoro-2-hydroxy-2-methylpropanamide or N-(6-chloro-3-phenylsulfonyl)phenyl-3,3,3-trifluoro-2-hydroxy-2-methylpropanamide.

A preferred group of compounds of formula I are compounds of formula Ib, wherein Ar is phenyl or 4-pyridyl; Y is sulfonyl; A—B is NHCO; $R^9$ is fluoro, chloro, cyano, nitro, methyl or methoxy; and $R^{10}$ and $R^{11}$ are hydrogen; or Ar is phenyl; Y is carbonyl; A—B is NHCO; $R^9$ is fluoro, chloro, cyano, nitro, methyl, hydroxy or methoxy; and $R^{10}$ and $R^{11}$ are hydrogen.

Because the compounds of Example 1, 4 and 6 are active and selective for the bladder without significant cardiovascular effects when dosed orally in the in vivo screen described hereinbelow, these compounds, individually and together, represent a preferred embodiment of the invention.

A compound of formula I can be made by processes which include processes known in the chemical arts for the production of structurally analogous compounds. Such processes are provided as further features of the invention and are illustrated by the following procedures in which the meanings of generic radicals are as given above unless otherwise qualified. Such a process can be effected, generally, (a) by deprotecting a protected compound having formula II wherein "Pg" is a suitable alcohol protecting group such as for example a benzyl group or a silyl protecting group; Examples of suitable reagents for deprotecting a compound of formula II when Pg is benzyl are (1) hydrogen in the presence of palladium-on-carbon catalyst, i.e. hydrogenolysis; or (2) hydrogen bromide or iodide; and when PG is a silyl protecting group are (1) tetrabutylammonium fluoride; or (2) aqueous hydrofluoric acid. The reaction can be conducted in a suitable solvent such as ethanol, methanol, acetonitrile, or dimethylsulfoxide and may conveniently be performed at a temperature in the range of −40 to 100° C.

When Y is carbonyl:

(b) by oxidizing a corresponding alcohol of formula I wherein Y is defined as CH(OH). Oxidizing agents such as bromine and pyridinium dichromate and solvents such as methanol and dichloromethane, respectively, may be employed. For example, a compound of formula Ia wherein E is ArY, D is hydrogen and Y is carbonyl may be prepared by oxidizing a corresponding compound of formula III.

(c) by deprotecting a corresponding compound of formula I wherein Y is a ketal protected carbonyl. A saturated aqueous acid such as oxalic or a mineral acid such as hydrochloric acid or sulphuric acid may conveniently be employed. The reaction may conveniently be performed at a temperature in the range of 0 to 100° C. in a solvent such as a lower alcohol (e.g., methanol or ethanol), or mixtures of solvent pairs such as water/dichloromethane, water/tetrahydrofuran, and water/acetone. For example, a compound of formula Ia wherein E is ArY, D is hydrogen and Y is carbonyl may be prepared by deprotecting a corresponding compound of formula IV.

(d) by treating a corresponding compound of formula I wherein ArY is defined as a leaving group such as for example bromo or iodo, with a tin compound having the formula Sn(Ar)$_4$ and carbon monoxide to effect carbonylative coupling, in the presence of a suitable catalyst such as bis(triphenylphosphine)palladium dichloride. The reaction may conveniently be performed at a temperature in the range of 0 to 100° C. and in a solvent such as tetrahydrofuran, 1,3-dimethyl-3,4,5,6-tetrahydro-2(1H)-pyrimidinone, or dimethyl sulfoxide. For example, a compound of formula Ia wherein E is ArY, D is hydrogen and Y is carbonyl may be prepared by subjecting a corresponding compound of formula V, wherein $G^1$ is a leaving group such as for example bromo or iodo, and a tin compound having the formula Sn(Ar)$_4$ to the above carbonylative coupling conditions.

(e) by treating a corresponding compound of formula I wherein ArY is defined as a leaving group such as for example bromo or iodo, with an aluminum compound having the formula Al(Ar)$_3$ and carbon monoxide to effect carbonylative coupling, in the presence of a suitable catalyst such as bis(triphenylphosphine) palladium dichloride. The reaction may conveniently be performed at a temperature in the range of 0 to 100° C. and in a solvent such as diethyl ether, benzene, toluene, or tetrahydrofuran. For example, a compound of formula Ia wherein E is ArY, D is hydrogen and Y is carbonyl may be prepared by subjecting a corresponding compound of formula V, wherein $G^1$ is a leaving group such as for example bromo or iodo, and an aluminum compound having the formula Al(Ar)$_3$ to the above carbonylative coupling conditions.

When Y is sulfonyl:

(f) by treating a corresponding compound of formula I wherein ArY is defined as a leaving group such as for example bromo or iodo with a compound of formula ArSO$_2^-$Na$^+$ in the presence of a catalyst such as cuprous oxide. The reaction may conveniently be performed at a temperature in the range of 30 to 200° C. and in a solvent such as N,N-dimethylformamide, 1,3-dimethyl-3,4,5,6-tetrahydro-2(1H)-pyrimidinone, dimethyl sulfoxide, or ethylene glycol. For example, a compound of formula Ia wherein E is ArY, D is hydrogen and Y is sulfonyl, may be prepared by treating a corresponding compound of formula V, wherein G$^1$ is a leaving group such as for example bromo or iodo, with a compound of formula ArSO$_2^-$Na$^+$ as described above.

When Y is sulfinyl or sulfonyl and A—B is any of the values defined above, except SCH$^2$ or NHCH$_2$:

(g) by oxidizing a corresponding sulfide. Suitable oxidizing agents include potassium permanganate, oxone, sodium periodate, and hydrogen peroxide. The reaction may be conducted in a suitable solvent such as diethyl ether, methanol, ethanol, water, acetic acid, and mixtures of two or more of the aforementioned. The reaction may conveniently be performed at a temperature in the range of –40 to 70° C.

When A—B is NHCO:

(h) by coupling an aniline of formula VI with an acid of formula VII wherein G is a hydroxy group. The reaction can be conducted in a suitable solvent and in the presence of a suitable coupling reagent. Suitable coupling reagents generally known in the the art as standard peptide coupling reagents can be employed, for example thionyl chloride, carbonyldiimidazole and dicyclohexylcarbodiimide, optionally in the presence of a catalyst such as dimethylaminopyridine or 4-pyrrolidinopyridine. Suitable solvents include dimethylacetamide, dichloromethane, benzene, tetrahydrofuran, and dimethylformamide. The coupling reaction may conveniently be performed at a temperature in the range of –40 to 40° C.;

(i) by reacting an amide of formula VIII with a base sufficiently basic (e.g., a lithium dialkylamide such as lithium diisopropyl amide) to yield an amide dianion, followed by treatment of the dianion with oxygen in the presence of a reducing agent (e.g., such as triphenyl phosphine). The sequence of reactions may conveniently be performed at a temperature in the range of –100 to –20° C., preferably at a temperature in the range of –20 to 50° C., in a suitable solvent such as tetrahydrofuran or diethyl ether.

(j) by reacting a corresponding compound of formula IX, wherein Hal indicates a halogen substituent (e.g., the corresponding chloride), with a corresponding alkali metal amide dianion having formula X wherein M is an alkali metal such as sodium or lithium; The reaction may conveniently be performed at a temperature in the range of –40 to 100° C. and in a suitable solvent such as dimethylformamide, dimethylsulfoxide, or tetrahydrofuran.

When Y is sulfonyl and A—B is NHCH$_2$:

(k) by reacting a corresponding compound of formula XI, wherein OR$^4$ is an alcohol residue such as for example methoxy or ethoxy, with a Grignard compound of formula R$^2$MgBr or R$^2$MgCl; The reaction may conveniently be performed at a temperature in the range of –100 to 20° C., preferably at a temperature in the range of –20 to 20° C., in a suitable solvent such as tetrahydrofuran or diethyl ether.

When A—B is trans-vinylene or ethynylene and Y is sulfonyl:

(l) by treating a corresponding compound of formula XII with a compound of formula R$^2$M wherein M is an alkali metal (such as lithium) or a Grignard compound of formula R$^2$MgBr or R$^2$MgCl. The reaction may conveniently be performed at a temperature in the range of –100 to 0° C. and in a solvent such as tetrahydrofuran, diethyl ether, or 1,2-dimethoxyethane.

When A—B is ethynylene:

(m) by coupling a corresponding compound of formula XIII, wherein L is a leaving group such as bromo, iodo, or triflate, with a corresponding acetylene of formula XIV, in the presence of a catalyst such as a combination of cuprous iodide and bis(triphenylphosphine) palladium dichloride or palladium(II) acetate. The reaction can be conducted in an inert solvent such as tetrahydrofuran, benzene, or toluene, or in a basic solvent such as diethylamine (DEA) or triethylamine (TEA), and at a temperature in the range of –20 to 110° C.

(n) by reacting a corresponding alkyne of formula XV with a base such as lithium diisopropylamide (LDA), n-butyllithium or tert-butyllithium, followed by treatment with a ketone of formula R—CO—R . The reaction may conveniently be performed at a temperature in the range of –100 to –40° C. preferably at a temperature in the range of –70 to –40° C. and in a solvent such as tetrahydrofuran, diethyl ether, or 1,2-dimethoxyethane.

When A—B is trans-vinylene:

(o) by reducing a corresponding acetylene of formula XVI with a suitable reducing agent, for example lithium aluminum hydride. The reaction can be conducted in a suitable solvent such as tetrahydrofuran or diethyl ether, and at a temperature in the range of 0 to 50° C. (p) and R$^3$ is CF$_3$, by treating a corresponding trans-vinylene compound of formula XVII with an organo-lithium compound of formula R$^2$Li. The reaction can be conducted at a temperature of in the range of -100 to 25° C. and in a solvent such as tetrahydrofuran, diethyl ether, or 1,2-dimethoxyethane. (q) by dehydration of a diol of formula XVIII in the presence of an acid catalyst (for example p-toluenesulfonic acid), neat or with a solvent such as toluene or dichloromethane, and at a temperature in the range of 0 to 200° C. preferably a temperature in the range of 20 to 100° C. (r) by base catalyzed opening of an epoxide of formula XIX. The opening may be carried out in a suitable organic solvent such as for example, ethers, alcohols, or toluene; ethers such as tetrahydrofuran are preferred. Suitable bases include for example sodium hydroxide, sodium methoxide, potassium tert-butoxide or sodium hydride. A basic aqueous solution may conveniently be employed. A preferred base is aqueous sodium hydroxide. The opening may be carried out at a temperature in the range of –50° C. to 100° C., preferably at a temperature in the range of 0 to 50° C., such as for example room temperature.

(s) by dehydration of a diol of formula XX using a suitable base. The dehydration may be carried out in a suitable organic solvent, for example, ethers such as tetrahydrofuran. The dehydration may be carried out at a temperature in the range of –78° C. to 100° C., preferably at a temperature in the range of 0 to 50° C., such as for example room temperature.

When A—B is NHCH$_2$:
  (t) by reducing a corresponding compound of formula I in which A—B is NHCO, with a suitable reducing agent such as lithium aluminum hydride or borane. The reaction can conveniently be carried out at a temperature in the range of 0° C. to reflux, in solvents such as for example diethyl ether, tetrahydrofuran, or 1,2-dimethoxyethane.

When A—B is OCH$_2$ or SCH$_2$:
  (u) by reacting an ethylene oxide of formula XXI with a corresponding compound of formula XXII (wherein J is, correspondingly, oxygen or sulfur), in the presence of a base such as for example sodium hydride. The reaction can be conducted at reflux in a solvent such as methylene dichloride.

When A—B is OCH$_2$, NHCH$_2$ or SCH$_2$:
  (v) by heating a corresponding compound of formula XXIII, wherein R$^5$ is correspondingly, OH, NH$^2$ or SH in the presence of a base such as for example an alkali metal hydride at a temperature in the range of 20° C. to about reflux, in a solvent such as N,N-dimethylformamide.

When Y is sulfonyl, A—B is vinylene or ethynylene, and R$^1$=R$^2$:
  (w) by treating a corresponding compound of formula XXV, wherein OR$^6$ is an alcohol residue such as for example methoxy or ethoxy, with a compound of formula R$^2$M wherein M is an alkali metal (such as lithium) or a Grignard compound of formula R$^2$MgBr or R$^2$MgCl. The reaction may conveniently be performed at a temperature in the range of –100 to 0° C. in a suitable solvents such as for example tetrahydrofuran, diethyl ether, or 1,2-dimethoxyethane.
  (x) for a compound of formula I which bears a hydroxy substituent on an aryl or heteroaryl group, by cleaving the alkyl ether or acyloxy ester of a corresponding compound of formula I which bears a lower alkoxy or lower acyloxy substituent on an aryl or heteroaryl group. Convenient methods include, for example, the cleavage of a methoxy group using boron tribromide and the cleavage of a t-butoxy group using trifluoroacetic acid.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples. In the discussion which follows, "Ar" refers to an unsubstituted or substituted phenyl group or heteroaryl group as previously defined.

In general, a compound of formula II may be made by treating a corresponding compound of formula XXII (wherein J is, correspondingly, oxygen, sulfur, or NH) with a corresponding compound of formula XXIV (wherein Pr is a protective group such as silyl and X is a suitable leaving group such as for example mesylate or triflate), in the presence of a base such as an alkali metal hydride (e.g., sodium hydride), in a solvent such as tetrahydrofuran, N,N-dimethylformamide, dimethyl sulfoxide, or 1,3-dimethyl-3,4,5,6-tetrahydro-2(1H)-pyrimidinone, and at a temperature of about 20° C. to about reflux.

Compounds of formulae II, III, VIII and XI, wherein A—B is NHCO, may be made in a manner analogous to that described in procedure (h) above for making an amide of formula II; that is, by coupling a corresponding aniline with a corresponding acid. Thus, to make a protected amide of formula II, a corresponding aniline of formula VI may be coupled with an acid of formula VII wherein the group corresponding to G is OPg. The protected acid may be made by a conventional procedure, for example by (i) esterifying an acid of formula VII wherein G is hydroxy by means of a conventional esterification procedure such as reaction with a lower alcohol (e.g., methanol) in the presence of an acid catalyst (for example sulfuric acid); (ii) reaction of the ester thus formed with an agent which provides the protecting group Pg, such as benzyl chloride (to provide a benzyl protecting group) or any of the conventional silylating agents known and used for such purpose (such as 2-trimethylsilylethoxymethyl chloride, SEM, in the presence of a suitable base such as sodium hydroxide or triethylamine optionally in the presence of a catalyst such as DMAP); and (iii) cleavage of the ester group under mild alkaline conditions (i.e., employing a base such as potassium carbonate) to yield the desired protected acid.

A compound of formula II wherein A—B is OCH$_2$, SCH$_2$ or NHCH$_2$ may be made by protecting a corresponding alcohol made in essentially any earlier stage of synthesis, for example an alcohol of formula V, XIV or XVI. The alcohol may be treated with a compound which reacts to form a trialkylsilyl (e.g. trimethylsilyl) group, such as trimethylsilyl chloride or trimethylsilyl triflate, in the presence of a base such as sodium hydride, diisopropylethylamine or triethylamine. A preferred base is diisopropylethylamine. Alternatively, if an ester protecting group is desired the alcohol may be reacted with an acid chloride of formula R$^5$COCl or an acid anhydride of formula (R$^5$CO)$_2$O wherein R$^5$ is a lower alkyl or aryl group. The reaction may be conducted in a solvent such as dichloromethane, in the presence of a base such as TEA and dimethylaminopyridine (DMAP), and at a temperature of –40 to about 25° C.

A compound of formula IV, wherein A—B is ethynylene, may be made by reacting a corresponding compound of formula XXVI with a base such as an alkyllithium (for example, butyllithium) followed by addition of a ketone having the formula R$^2$—CO—R$^3$. The reaction may be conducted at a temperature of from about –100 to about –40° C. and in a solvent such as tetrahydrofuran, dimethyl ether, or 1,2-dimethoxyethane.

A compound of formula IV, wherein A—B is trans-vinylene, may be made by reducing a corresponding compound of formula IV, wherein A—B is ethynylene, with a suitable reducing agent such as lithium aluminum hydride or sodium bis(2-methoxyethoxy)aluminum, in a solvent such as tetrahydrofuran and at room temperature.

A compound of formula XXVI may be made by treating the corresponding ketone with 1,3-propanediol in the presence of an acid catalyst such as p-toluenesulfonic acid (TsOH) and in a refluxing solvent such as toluene.

A compound of formula XXVII wherein A—B is ethynylene, may be made by (1) treating a corresponding compound of formula XIII wherein L is bromo with a protected acetylene such as trimethylsilylacetylene in the presence of a catalyst such as a combination of cuprous iodide and bis(triphenyl-phosphine)palladium dichloride in a solvent such as diethylamine, thereby making a corresponding compound of formula XXVIII, wherein A—B is ethynylene and Ps is a silyl protecting group, followed by (2) removal of the silyl protecting group with a base such as an alkali metal (e.g. sodium hydroxide) in a solvent such as methanol.

A compound of formula V wherein G$^1$ is halo, may be made by (1) treating a corresponding compound of formula V, wherein $G^1$ is nitro, with a reducing agent such as tin(II) chloride, in the presence of an aqueous acid such as acetic acid to obtain the corresponding amine, followed by (2) treating the amine with a combination of nitrous acid and sulfuric acid to effect diazotization, and thereafter (3) treating the diazotized compound with a corresponding copper(I) halide such as for example cuprous bromide, CuBr.

A compound of formula XII, wherein A—B is ethynylene, may be made by treating a corresponding compound of formula XXVIII, wherein Ps is trimethylsilyl, with a fluoride base (for example, TBAF) and an acid chloride of formula $R^3$—CO—Cl, thereby making the desired compound.

A compound of formula XXV, wherein A—B is ethynylene, may be made by treating a corresponding compound of formula XXVIII, wherein A—B is ethynylene and Ps is trimethylsilyl, with a base (for example, TBAF) and an alkyl carbonate of formula $(R\ 6O)_2CO$ or an alkyl chloroformate of formula $ClCOOR^6$, to give a corresponding compound of formula XXV wherein $OR^6$ is an alcohol residue, for example methoxy or ethoxy.

A compound of formula XXV, wherein A—B is ethynylene, can alternatively be made by treating a corresponding compound of formula XXVIII, wherein A—B is ethynylene and Ps is trimethylsilyl, with TBAF and carbon dioxide and esterified with a lower alcohol of formula $R^6OH$.

A compound of formula XIII, wherein L is halo, may be made by treating a corresponding compound of formula XIII, wherein L is nitro, with iron dust and concentrated hydrochloric acid in 95% ethanol to reduce the nitro group and thereby form the corresponding amine. The amine may then be treated with a nitrite (such as t-butyl nitrite) to form the corresponding diazonium salt which may in turn be treated with a copper(I) salt (such as copper(I) bromide or copper(I) chloride). The diazotization and displacement reactions may be conducted in a solvent such as acetonitrile and at a temperature of from 0 to 25° C.

A compound of formula XIV may be made by reacting a corresponding ketone having the formula $R^2$—CO—$R^3$ with an alkali metal acetylide (for example lithium acetylide) or alkaline earth metal acetylide (for example magnesium acetylide). The reaction may be conducted in a solvent such as tetrahydrofuran, diethyl ether, or 1,2-dimethoxyethane and at a temperature of about −100 to about 25° C.

A compound of formula XV may be made by reacting a corresponding compound of formula XIII, wherein L is halo, with trimethylsilylacetylene in the presence of a catalyst such as a combination of bis(triphenylphosphine)palladium dichloride and copper(I) iodide in diethylamine or triethylamine, followed by treatment with a base (for example, an alkali metal hydroxide such as sodium or lithium hydroxide) in a lower alcohol as solvent to effect removal of the trimethylsilyl group.

Compounds of formula XVII may be made using procedures similar to those described in Morris et al., J. Med. Chem., 34, 447–455, (1991).

A compound of formula XXI may be made by treating a corresponding ketone having the formula $R^2$—CO—$R^3$ with the ylide derived from the reaction of a trimethylsulfonium salt (such as trimethylsulfonium iodide) with a base (such as an alkali metal hydroxide). The reaction may be conducted in a one-pot process employing a solvent such as dichloromethane.

A compound of formula XXII, wherein J is oxy, may be made by diazotizing a corresponding aniline of formula XIII, wherein L is amino, as previously discussed, and heating in dilute sulfuric acid to form the corresponding phenol. The corresponding thiophenol may be formed by reacting an excess of methanethiol in the presence of sodium hydride with a corresponding compound of formula XIII wherein L is a leaving group such as for example chloro.

A compound of formula XXIII may be made by treating a corresponding compound of formula XIII wherein L is a halo group with a corresponding compound of formula XXIV, wherein X is hydroxy, thiohydroxy, or amino, and Pg is hydrogen. The reaction may conveniently be carried out in the presence of a catalyst such as copper bronze and a base such as an alkali metal hydride. The reaction may be conducted at reflux in a solvent such as tetrahydrofuran.

A compound of formula XXIV, wherein X is mesylate, may be made by (1) esterifying an acid of formula VII wherein G is hydroxy; (2) protecting the alcohol G, by treating with for example trimethylsilyl chloride in a solvent such as dichloromethane and at a temperature of from about −78 to about 25° C.; (3) treating the protected compound thus obtained with a suitable reducing agent such as lithium aluminum hydride in a solvent such as diethyl ether or tetrahydrofuran and at a temperature of about 0 to about 25° C., thereby reducing the carbonyl group to methylene; followed by (4) treating the reduced product with trifluoromethylsulfonic anhydride in the presence of a base such as triethylamine, in a solvent such as dichloromethane, and at a temperature of about −78° C. to about 25° C.

An epoxide of formula XIX may be prepared from a diol of formula XX using a suitable dehydrating agent, for example bis[α,α-bis(trifluoromethyl)benzenemethanolato] diphenylsulphur.

A diol of formula XX may be prepared from a compound of formula I, wherein A—B is CHCO, by reduction. The reduction may be carried out using a suitable reducing agent, for example a hydride, such as sodium borohydride.

A compound of formula I, wherein A—B is CHCO, may be prepared from a compound of formula XIII, wherein L is methyl, by deprotonation and treatment with an amide of formula XXIX, in which $R^7$ and $R^8$ are each independantly lower alkyl, or in which $R^7$ and $R^8$ when taken together with the atoms to which they are attached form a 5–7 membered ring. The deprotonation of the toluene may be carried out with a suitable base, for example lithium diisopropyl amide. The reaction may be carried out in a suitable organic solvent, for example, an ether such as tetrahydrofuran. The reaction may be carried out at a suitable temperature, for example a temperature in the range of −78° C. to 100° C.

An amide of formula XXIX may be prepared from an acid of formula VII, wherein G is hydroxy, or a reactive derivative thereof, by reaction with the corresponding amine.

A diol of formula XVIII may be prepared by (a) treating a ketone of formula XIII, wherein L is acetyl, with a base such as LDA, lithium hexamethyldisilazide(LHMDS), or tetramethylpiperadide, in a solvent such as tetrahydrofuran, diethyl ether, or 1,2-dimethoxyethane, followed by addition of a ketone having the formula $R^2$—CO—$R^3$ (aldol condensation), and at a temperature of about −100 to about 25° C., followed by (b) reduction of the carbonyl group to alcohol with a reducing agent such as sodium borohydride or lithium aluminum hydride at a temperature of from about 0 to about 25° C.

It is noted that many of the starting materials for synthetic methods as described above are commercially available and/or widely reported in the scientific literature.

In cases where compounds of formula I are sufficiently basic or acidic to form stable acid or basic salts, administration of the compound as a salt may be appropriate, and pharmaceutically acceptable salts may be made by conventional methods such as those described following. Examples of suitable pharmaceutically acceptable salts are organic acid addition salts formed with acids which form a physiologically acceptable anion, for example, tosylate, methanesulfonate, acetate, tartrate, citrate, succinate, benzoate, ascorbate, α-ketoglutarate, and α-glycerophosphate. Suitable inorganic salts may also be formed such as sulfate, nitrate, and hydrochloride.

Pharmaceutically acceptable salts may be obtained using standard procedures well known in the art, for example by reacting a sufficiently basic compound of formula I (or its ester) with a suitable acid affording a physiologically acceptable anion. It is also possible with most compounds of the invention to make a corresponding alkali metal (e.g., sodium, potassium, or lithium) or alkaline earth metal (e.g., calcium) salt by treating a compound of formula I (and in some cases the ester) with one equivalent of an alkali metal or alkaline earth metal hydroxide or alkoxide (e.g. the ethoxide or methoxide in aqueous medium followed by conventional purification techniques.

In vivo hydrolyzable esters of compounds of the invention may be made by coupling with a pharmaceutically acceptable carboxylic acid or an activated derivative thereof. For example, the coupling may be carried out by treating a compound of formula I with an appropriate acid chloride (for example, acetyl chloride, propionyl chloride, or benzoyl chloride) or acid anhydride (for example, acetic anhydride, propionic anhydride, or benzoic anhydride) in the presence of a suitable base such as triethylamine. Those skilled in the art will appreciate that other suitable carboxylic acids (including their activated derivatives) for the formation of in vivo hydrolyzable esters are known to the art and these are also intended to be included within the scope of the invention. Catalysts such as 4-dimethylaminopyridine may also be usefully employed.

When used to treat urinary incontinence, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention.

The compositions may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous, intravesicular, subcutaneous or intramuscular injection or infusion; or in the form of a patch for transdermal administration.

Treatment using a compound according to the invention may be remedial or therapeutic as by administering a compound following the onset or development of urinary incontinence in a patient. Treatment may also be prophylactic or prospective by administering a compound in anticipation that urinary incontinence may develop, for example in a patient who has suffered from incontinence in the past.

According to a further aspect, the invention provides the use of a compound of formula I, as defined hereinabove, in the manufacture of a medicament for the treatment of urinary incontinence.

It has also unexpectedly been found that compounds according to the invention are potassium channel openers. It is known that by functioning to open potassium channels, potassium channel opening compounds may thereby function to relax smooth muscle.

Because compounds according to the invention function to open cell potassium channels, they may also be useful as therapeutic agents in the treatment of other conditions or diseases in which the action of a therapeutic agent which opens potassium channels is desired or is known to provide amelioration. Such conditions or diseases include hypertension, asthma, peripheral vascular disease, right heart failure, congestive heart failure, angina, ischemic heart disease, cerebrovascular disease, renal cholic, disorders associated with kidney stones, irritable bowel syndrome, male pattern baldness, premature labor, and peptic ulcers.

The dose of compound of formula I which is administered will necessarily be varied according to principles well known in the art taking account of the route of administration, the severity of the incontinence condition, and the size and age of the patient. In general, a compound of formula I will be administered to a warm blooded animal (such as man) so that an effective dose is received, generally a daily dose of above 0.005, for example in the range of about 0.01 to about 10 mg/kg body weight.

It will be apparent to those skilled in the art that a compound of formula I may be co-administered with other therapeutic or prophylactic agents and/or medicaments that are not medically incompatible therewith. Compounds within the scope of the invention have not been found show any indication of untoward side-effects in laboratory test animals at several multiples of the minimum effective dose.

The actions of compounds of formula I as therapeutic agents for the treatment of urinary incontinence may be shown using suitably designed in vitro tests, such as the one described following.

Male albino Hartley guinea pigs (450–500 g) are sacrificed by cervical dislocation. The lower abdominal cavity is opened and the urinary bladder located. Once located, it is cleaned of surrounding connective and adipose tissue. The two pelvic nerves on the ventral surface of the bladder are cut away, then the bladder body is removed above the entrance of the ureters. The bladder is washed in Krebs-Henseleit buffer solution (composition (mM): NaCl 118.0, KCl 4.7, $MgSO_4$ 1.2, $KH_2PO_4$ 1.2, $CaCl_2$ 2.5, $NaHCO_3$ 25 and D-Glucose 11.1) and then placed on a buffer-soaked gauze in a petri dish. The dome of the bladder is cut off and discarded.

A mid-ventral longitudinal cut is made with scissors and the bladder laid flat on the gauze. Strips are cut from the dome edge and the base edge and discarded. The remaining detrusor mid-section is cut into two latitudinal (horizontal) strips, with an approximate width of 2.0 mm. These two strips are cut in half at the mid-dorsal section, creating four strips of similar dimensions. Each strip thus contains both dorsal and ventral portions of the bladder.

Each individual strip is tied at one end directly to a glass support rod and a length of 4-0 black braided silk suture is tied to the other end. The glass rods are secured in 20 ml tissue baths and the length of suture attached to a force-displacement transducer (Grass model FT03).

The tissues are bathed in Krebs-Henseleit buffer solution. The bathing solution is warmed to 37° C. and gassed with 5% $CO_2$ and 95% $O_2$, with vigorous bubbling. The solution should have a pH value close to 7.4.

The transducers are connected to a polygraph (Grass model 7E) and interfaced with a Modular Instrument Micro 5000 signal processing system and Biowindow Data Acquisition Software (run on Microsoft OS/2 with an IBM-compatible PC).

The polygraph is calibrated at 5mV/cm and calibration checked for linearity with weights of 5 and 0.5 grams.

The tissue is incubated in the buffer for 15 minutes without preload tension, then 30 minutes with tension applied. The preload tension applied is 2 grams that relaxes to approximately 1 gram. The tissue is washed at 15 minute intervals, with tension adjusted to 2 grams just prior to washing. After this 45 minute equilibration period, a priming dose of 15 nM KCl (total concentration in bath) is applied. The tissue is washed after 10 minutes and washed twice more at 15 minute intervals with tension adjusted to 2 grams before each washing.

When the tissue relaxes to a steady state after the final washing, 15 mM KCl is again dosed. Once the tissue reaches a steady state the base line data are acquired on the Biowindows Data Acquisition System. This is done by averaging 5 minutes of data, sampling at 32 Hz. Once the baseline is acquired, the experimentalcompounds are dosed in a cumulative manner in half log unit increments. The contact time for each dose is 10 minutes with the final 5 minutes being the period of time that the dose response data are acquired. If 30 $\mu$M of the test compound does not abolish detrusor mechanical activity, then 30 $\mu$M cromakalim is dosed to establish a maximum response. The effects of the compounds are expressed as % of maximum relaxation of agonist induced tension.

In general, compounds of the invention demonstrate significant acitivity in the above described test at a concentration of 30 micromolar or less. Preferred compounds typically exhibit an $IC_{50}$ on the order of 30 micromolar or less in the test. For example, the compound of Example 2 has an $IC_{50}$ of 11.38 in the above test. $IC_{50}$ is a well understood term and means the concentration of test compound which causes a 50% decrease in the in vitro contraction of the bladder tissue described in the above test.

The following is a description of a test in vivo which is complimentary to the above described test and which may be used to ascertain if a test compound is active and, additionally, if the test compound exhibits selectivity for the bladder without significant cardiovascular effects when dosed orally.

Male Wistar rats (400–500 g) were anesthetized with 50 mg/kg Nembutal, i.p. For each rat, the abdominal region and the front and back of the neck were shaved and povidone-iodine was applied to the skin. For carotid catheterization, the left carotid artery was exposed via a small ventral cervical incision. The exposed area was flushed with a 2% lidocaine HCl solution to relax the vessel. The catheter, filled with 0.9% saline, was introduced approximately 2.4 cm into the artery so that its tip resided in the aortic arch. The distal end of the catheter was exteriorized at the nape of the neck, filled with heparin (1000 units/ml) and heat sealed. For bladder catheterization, the bladder was exposed through a midline abdominal incision. A trocar was passed through the abdominal muscle about 1 cm from the upper end of the incision and then tunneled subcutaneously to emerge through the skin at the back of the neck. A saline-filled catheter was passed through the trocar. A small opening in the bladder dome was created with an Accu-Temp cautery. The catheter was placed into the bladder and secured with a 4-0 silk ligature. The catheter was flushed with saline and patency was noted. The external end of the catheter was heat-sealed to prevent urine leakage. The abdominal muscles and the skin were sutured. Both catheters were threaded through a stainless steel anchor button (Instech), which was then sutured to the subcutaneous muscle at the point of exteriorization. The skin was sutured closed over the button. The animals were allowed to recover from anesthesia.

24–48 hours after surgery, each rat was placed in a metabolism cage and connected via the anchor button to an Instech spring tether and swivel system to protect the catheters from damage and to allow the animal free movement in the cage. The carotid catheter was connected to a Gould P23XL pressure transducer for blood pressure measurement. The bladder catheter was connected to a pump for saline infusion and to a pressure transducer by means of PE50 tubing and a 4-way stopcock. A toploading balance with a collection cup was placed under the cage for urine output measurement.

The rats were weighed, orally sham-dosed (dosing needle introduced, but no fluid expelled), and transvesical saline infusion (.18 ml/min) was begun and continued throughout the experiment. Variations in blood pressure, heart rate, intravesical pressure and urine output were recorded on either a Grass Polygraph or a Gould TA4000 recording system. The animals were allowed to equilibrate until the micturition pattern became consistent (approx. 45–90 min.). At this point, a basal level of each experimental parameter was recorded and the rats were administered by oral gavage the appropriate dose of compound (in a 75% PEG 400—saline vehicle) in concentrations such that the volume was 1 ml/kg body weight. The effects of the compounds on experimental parameters were followed for five hours after administration.

Experimental results for both the interval between contractions and also heart rates were expressed as the mean±S.E.M. (Standard Error of Measures) % change from basal level, with each animal serving as its own control. MAP is expressed as mean±S.E.M mm Hg change from basal level.

Compounds according to the invention are active in one or more of the above-described tests. For example, the compounds of Examples 1, 4 and 6 are active and selective for the bladder without significant cardiovascular effects, when dosed orally at 3 mg/kg in the above in vivo screen.

The invention will now be illustrated by the following non-limiting examples in which, unless stated otherwise:

(i) temperatures are given in degrees Celsius (°C.); operations were carried out at room or ambient temperature, that is, at a temperature in the range of 18–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which can be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (dimethyl sulfoxide-$d_6$) as solvent; coupling constants (J) are given in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars; (xi) solvent ratios are given in volume:volume (v/v) terms; and (xii) mass spectra (MS) were run with an electron energy of 70 electron volts in the chemical ionization (CI) mode using a direct exposure probe; where indicated ionization was effected by electron mpact (EI) or fast atom bombardment (FAB); values for m/z are given; generally, only ions which indicate the parent mass are reported.

EXAMPLE 1

N-(4-Benzoyl-2-methylphenyl)-3,3,3-trifluoro-2-hydroxy-2-methylpropanamide

To a solution of 3,3,3-trifluoro-2-hydroxy-2-methylpropanoic acid (1.11 g) in N,N-dimethylacetamide (15 mL) at −20° C. was added thionyl chloride (0.84 g) and the mixture was allowed to stir at −10 to −15° C. for 1 hour. 4-Amino-3-methylbenzophenone (1.00 g) was added in one portion and the reaction mixture was stirred at room temperature overnight. The mixture was poured into water and the resultant gummy solid was collected by filtration. The solid was dissolved in methylene chloride, dried and evaporated to give a brown oil. Chromatography, with diethyl ether:dichloromethane (2:98) as the eluent, gave a white foam which was stirred with hexane for two hours. The title compound was collected by filtration as a white solid (1.04 g); mp 123–124° C.; MS: m/z=352(M+1); NMR: 1.61 (s,3), 2.28 (s,3), 7.54–7.61 (m,3) 7.66–7.74 (m,6) 9.73 (s,1). Analysis for $C_{18}H_{16}F_3NO_3$: Calculated: C, 61.54; H, 4.59; N, 3.99; Found: C, 61.53; H, 4.73; N, 4.01.

EXAMPLE 2

N-(4-Benzoyl-2-fluorophenyl)-3,3,3-trifluoro-2-hydroxy-2-methylpropanamide.

To a solution of 3,3,3-trifluoro-2-hydroxy-2-methylpropanoic acid (4.51 g) in N,N-dimethylacetamide (60 mL) at −20° C. was added thionyl chloride (3.39 g) and the mixture was allowed to stir at −10 to −15° C. for 1 hour. 4-Amino-3-fluorobenzophenone (4.00 g) was added in one portion and the reaction mixture was stirred at room temperature overnight. The mixture was poured into water and the aqueous solution was decanted. The remaining oily precipitate was dissolved in dichloromethane, dried, and evaporated to yield a tan solid. Recrystallization from dichloromethane and hexanes yielded the title compound as a white solid (5.43 g); mp 138–139° C.; MS: m/z=356(M+1); NMR: 1.62 (s,3), 7.56–7.64 (m,4), 7.70 (d,1, J=6.5), 7.75 (d,2, J=8.0), 7.82 (s,1), 8.01 (t,1, J=7.9), 9.39 (s,1). Analysis for $C_{17}H_{13}F_4NO_3$: Calculated: C, 57.47; H, 3.69; N, 3.94; Found: C, 57.51; H, 3.60; N, 3.93.

The intermediate 4-Amino-3-fluorobenzophenone was prepared as follows.

To stirred polyphosphoric acid (125 g) at 90° C. was added benzoic acid (18.32 g) and 2-fluoroaniline (8.33 g) and the bath temperature was raised to 2000 for 1 hour. The heating bath was removed and the stirred mixture was treated cautiously with water (60 mL). The mixture was stirred at 140–160° C. for 1 hour, the heating bath was removed, and hydrochloric acid was added (3 N, 50 mL). The mixture was poured into water (750 mL) and filtered through diatomaceous earth with a dichloromethane wash. The filtrate was made basic with 15% sodium hydroxide and the mixture was again filtered through diatomaceous earth with a dichloromethane wash. The combined dichloromethane extracts were washed (saturated aqueous sodium bicarbonate), dried, filtered, and evaporated. Chromatography, with diethyl ether:hexanes (gradient, 10:90 to 50:50) as the eluent, followed by recrystallization from hexanes, yielded the aniline as a light yellow solid (7.48 g); mp 83–85° C.; MS: m/z=216(M+1); NMR (400 MHz): 6.27 (broad s,2), 6.80 (t,1, J=8.6), 7.36 (q,1, J=8.4, 1.9), 7.41 (q,1, J=12.4, 1.9), 7.49–7.51 (m,2) 7.60–7.63 (m,3). Analysis for $C_{13}H_{10}FNO$: Calculated: C, 72.55; H, 4.68; N, 6.51; Found: C, 72.51; H, 4.82; N, 6.42.

EXAMPLE 3

3,3,3-Trifluoro-2-hydroxy-2-methyl-N-(3-phenylsulfonyl-6-chlorophenyl)propanamide To a solution containing 3,3,3-trifluoro-2-hydroxy-2-methylpropanoic acid (2.00 g) in N,N-dimethylacetamide (40 mL) cooled to −20° C. was added thionyl chloride (1.50 g) and the mixture was stirred for 1.0 hour. 6-chloro-3-phenylsulfonylaniline (2.42 g) was added in one portion and mixture was stirred for 48 hours at room temperature. The reaction mixture was poured into aqueous sodium hydroxide (1.0 N, 250 mL) and extracted with ethyl acetate. The combined ethyl acetate extracts were washed (aqueous sodium hydroxide, brine) and evaporated. Chromatography, with hexane:ethyl acetate as the eluent (4:1 then 2:1) yielded the title compound as a white solid (1.25 g); mp: 79–80° C.; NMR (250 MHz): 1.61 (s,3), 7.69 (m,3), 7.82 (m,2), 7.94 (d,1, J=9), 7.98 (m,2), 8.52 (s,1), 9.93 (s,1); MS: m/z=408 (M+1). Analysis for $C_{16}H_{13}ClF_3NO_4S$: Calculated: C, 47.11; H, 3.19; N, 3.44; Found: C, 47.10; H, 3.28; N, 3.38.

The intermediate 6-chloro-3-(phenylsulfonyl)aniline was prepared as follows.

a. 2-Nitro-4-(phenylsulfonyl)chlorobenzene. Sodium nitrite (2.73 g), was added portionwise to concentrated sulfuric acid (50 mL) over a period of 10 minutes and the mixture was heated to 70° C. to give a homogeneous solution then cooled to room temperature. A suspension containing 2-nitro-4-(phenylsulfonyl)aniline (10 g) in glacial acetic acid (75 mL) was added to the sodium nitrite solution while maintaining an internal temperature below 40° C. The reaction temperature was maintained at 40° C. for 1 hour. The solution was poured into a solution containing cuprous chloride (7.48 g) and concentrated hydrochloric acid (75 mL) and heated to 80° C. for 1.0 hour. Water (500 mL) was added and the solution was cooled to 0° C. and stirred for 1.0 hour. The resultant pale yellow solid was collected by vacuum filtration and washed with water (3×50 mL). The yellow solid was washed with dichloromethane (3×150 mL), and the combined dichloromethane washes were dried and evaporated to give the chloro compound as a pale orange-yellow solid (10 g); mp 118–120° C.; NMR (250 MHz): 7.71 (m,3), 7.76 (d,1, J=8), 8.04 (m,3), 8.26 (dd,1, J=8, J=2), 8.67 (d,1, J=2); MS: m/z=298(M+1).

b. 6-Chloro-3-(phenylsulfonyl)aniline. 2-Nitro-4-(phenylsulfonyl)chlorobenzene (9.8 g) and stannous chloride dihydrate (33.5 g) were suspended in absolute ethanol (200 mL) and heated to 75° C. for 40 minutes. The solution was evaporated and the resulting material was cooled to 0° C. Water (100 mL) was added, and the pH was adjusted to 8.0 with aqueous sodium hydroxide. The resulting solids were removed by filtration and the aqueous filtrate was extracted with ethyl acetate. The combined ethyl acetate solutions were evaporated to give a brown solid. Chromatography, with dichloromethane as the eluent yielded the aniline as an orange solid (7.3 g); mp: 105–107° C.; 250 MHz NMR: 5.96 (s,2), 7.02 (dd,1 J=8, 2), 7.34 (d,1, J=2), 7.41 (d,1, J=8), 7.61 (m,3), 7.88 (d,2, J=7); MS: m/z=268(M+1).

EXAMPLE 4

3,3,3-Trifluoro-2-hydroxy-N-[2-methoxy-4-(4-pyridylsulfonyl)phenyl]-2-methylpropanamide.

To a stirred, cooled (−20° C.) solution of 3,3,3-trifluoro-2-hydroxy-2-methylpropanoic acid (1.35 g) in N,N-dimethylacetamide (20 mL) was rapidly added thionyl chloride (1.01 g) and the mixture (a precipitate formed after a few minutes) was stirred at −15 to −5° C. for 1 hour. 2-Methoxy-4-(4-pyridylsulfonyl)aniline (1.50 g) was then added in one portion and the mixture allowed to stir at room tmmperature overnight. The solution was poured into ice water (200 mL) and the resulting tan solid was collected and recrystallized from absolute ethanol to yield the title compound as a white solid (1.58 g); mp 220–222° C.; MS: 405(M+1); NMR (250 MHz): 1.53 (s,3,), 4.02 (s,3), 7.62 (d,1, J=1.9), 7.68 (dd,1, J=1.9, J=8.5), 7.92–7.95 (m,2,), 8.02 (s,1,), 8.46 (d,1, J=10) 8.80–8.89 (m,2,), 9.90 (s,1). Analysis for $C_{16}H_{15}F_3N_2O_5S$: Calculated: C, 47.53; H, 3.74; N, 6.93; Found: C, 47.56; H, 3.77; N, 6.76.

The starting 2-methoxy-4-(4-pyridylsulfonyl)aniline was prepared as follows:

a. 6-Nitro-3-(4-pyridylthio)anisole. 6-Nitro-3-chloroanisole (9.38 g) was added to a solution of 4-mercaptopyridine potassium salt [prepared by adding 4-mercaptopyridine (6.67 g) to a solution of potassium hydroxide (3.37 g) in methanol (30 mL) followed by evaporation of the methanol] and N,N-dimethylformamide (40 mL). After stirring for 1 hour, the mixture was heated at 110° C. for 4 hours and allowed to stand overnight. The reaction mixture was poured into ice-water (1 L), stirred for 15 minutes, and the yellow solid was filtered off. The solid was stirred with 3 N HCl (800 mL) for 1 hour, filtered, and the filter cake was washed with 3 N HCl then water. The filtrate was cooled in an ice-bath and made basic with 28% aqueous $NH_4OH$ to yield approximately 2 g of the sulfide. The filter cake was suspended in water (100 mL) with stirring and the mixture was made basic with saturated sodium bicarbonate and extracted with ethyl acetate. The organics were combined, dried, filtered and evaporated to give a yellow solid that was triturated with hexane and filtered to give additional sulfide (total yield 6.49 g); mp 97–100° C.; MS: m/z=263(M+1); NMR: 3.94 (s,3), 7.17 (dd,1, J=1.8, 8.4), 7.27–7.7.29 (m,2), 7.51 (d,1, J=1.8), 7.97 (d,1, J=8.4), 8.48–8.50 (m,2).

b. 6-Nitro-3-(4-pyridylsulfonyl)anisole. To a stirred solution of 6-nitro-3-(4-pyridylthio)anisole (6.49 g) and acetic acid (200 mL) was rapidly added a solution of potassium permanganate (4.69 g) in water (100 mL). After stirring for 1 hour, the mixture was clarified by the addition of solid sodium sulfite, diluted to a volume of 1 L with water and the resulting solid was collecyed. Recrystallization from absolute ethanol (300 mL) yielded the sulfone (3.43 g); mp 123–124° C.; NMR: 4.07 (s,3), 7.75 (dd,1, J=1.7, 8.4), 7.90 (d,1, J=1.7), 8.02–8.04 (m,2), 8.12 (d,1, J=8.4), 8.92–8.94 (m,2). Analysis for $C_{12}H_{10}N_2O_5S$: Calculated: C, 48.98; H, 3.42; N, 9.52; Found: C, 48.81; H, 3.45; N, 10.02.

c. 2-Methoxy-4-(4-pyridylsulfonyl)aniline. To a stirred slurry of 6-nitro-3-(4-phenylsulfonyl)anisole (3.40 g) and absolute ethanol (30 mL) was added stannous chloride dihydrate (13.0 g) in one portion. The mixture was heated at reflux for 50 minutes, poured onto ice-water (200 mL) and made basic with aqueous 15% NaOH. The mixture was extracted with ethyl acetate and the organics were evaporated to yield a white solid which was recrystallized from boiling absolute ethanol. After cooling the solid was filtered to yield the title aniline as a white solid (2.42 g); mp 163–165° C.; MS: m/z=265(M+1); NMR: 3.85 (s,3), 6.01 (s,2), 6.73 (d,1, J=8.4), 7.23 (d,1, J=2.0), 7.34 (dd,1, J=2.0, 8.4), 7.81–7.83 (m,2), 8.80–8.82 (m,2). Analysis for $C_{12}H_{12}N_2O_3S$: Calculated: C, 54.53; H, 4.58; N, 10.60; Found: C, 54.45; H, 4.54; N, 10.58.

EXAMPLE 5

3,3,3-Trifluoro-2-hydroxy-2-methyl-N-[2-nitro-4-(phenylsulfonyl)phenyl]propanamide A mixture of 3,3,3-trifluoro-2-hydroxy-2-methylpropanoic acid (1.00 g), 1,1'-carbonyldiimidazole (1.03 g) and dry tetrahydrofuran (25 mL) was heated, under $N_2$, at 45° C. in an ultrasound bath for 0.5 hours. 2-Nitro-4-(phenylsulfonyl)aniline (1.75 g) was added, the mixture was heated at 45° C. for 18 hours, poured onto water (350 mL) and extracted with $Et_2O$. The combined extracts were washed (brine), dried and evaporated to give an orange solid (3.01 g) that was purified by chromatographed, with chloroform as the eluent, to yield the title compound as a pale yellow solid (0.46 g); mp 191–192.5° C.; MS: m/z=419(M+1); NMR: 1.58 (s,3), 7.63–7.76 (m,3), 8.02–8.07 (d,3), 8.34 (dd,1, J=2.2, 8.6), 8.59 (s,1), 8.61 (d,1, J=2.3). Analysis for $C_{16}H_{13}F_3N_2O_6S$: Calculated: C, 45.94; H, 3.13; N, 6.70; Found: C, 45.95; H, 3.19; N, 6.53.

EXAMPLE 6

S-(−)-N-(4-Benzoyl-2-methylphenyl)-3,3,3-trifluoro-2-hydroxy-2-methylpropanamide.

To a stirred, cooled (−20° C.) solution of S-(−)-3,3,3-trifluoro-2-hydroxy-2-methylpropanoic acid (0.76 g) in N,N-dimethylacetamide (10 mL) was added thionyl chloride (0.57 g) and the mixture was stirred at −10 to −20° C. for 1 hour. 4-Amino-3-methylbenzophenone (0.68 g) was added in one portion and the reaction mixture was stirred at room temperature overnight. The mixture was poured into water and the aqueous solution was decanted from the precipated oil. The oil was dissolved in dichloromethane and the resulting solution was dried, evaporated and purified by chromatography, with dichloromethane and then diethyl ether:dichloromethane (5:95) as the eluents, to give the title compound as a white solid (0.40 g); mp 60–62° C.; NMR: 1.62 (s,3), 2.28 (s,3), 7.54–7.74 (m,9), 9.73 (s,1); MS: m/z=352(M+l). Analysis for $C_{18}H_{16}F_3NO_3.0.25H_2O$: Calculated: C, 60.76; H, 4.67; N, 3.93; Found: C, 60.68; H, 4.46; N, 3.89.

EXAMPLE 7

N-(4-Benzoyl-2-chlorophenyl)-3,3,3,-trifluoro-2-hydroxy-2-methylpropanamide

To a stirred, cooled (−20° C.) solution of 3,3,3-trifluoro-2-hydroxy-2-methylpropanoic acid (0.46 g) in N,N- dimethylacetamide (6 mL) was rapidly added thionyl chloride (0.35 g) and the mixture stirred at −15 to −20° C. for 1 hour. 3-Chloro-4-aminobenzophenone (0.45 g) was then added in one portion and the mixture allowed to stir at room temperature overnight. The solution was poured into ice water and filtered through diatomaceous earth. The diatomaceous earth was washed with methylene chloride, the organic solution dried and the solvent removed. Chromatography (eluent methylene chloride, then 5% ethyl acetate in methylene chloride) gave the title compound (0.31 g) as a white solid; mp 142–144° C. Analysis for $C_{17}H_{13}ClF_3NO_3$: Calculated: C, 54.92; H, 3.53; N, 3.77; Found: C, 54.89; H, 3.63; N, 3.68.

EXAMPLE 8

N-(4-Benzoyl-2-bromophenyl)-2-(difluoromethyl)-3,3,-difluoro-2-hydroxypropanamide Using a procedure similar to that described in Example 1, except replacing the 3,3,3-trifluoro-2-hydroxy-2-methylpropanoic acid with 3,3-difluoro-2-difluoromethyl-2-hydroxypropanoic acid and the 4-amino-3-methylbenzophenone with 4-amino-2-bromobenzophenone, the title compound was prepared; mp 128–132° C. Analysis for $C_{17}H_{12}BrF_4NO_3$: Calculated: C, 47.13; H, 2.79; N, 3.23; Found: C, 56.21; H, 2.95; N, 3.14.

The starting 4-amino-2-bromobenzophenone was prepared as follows.

Benzoic acid (13.26 g) and 2-bromoaniline (9.35 g) were added to polyphosphoricacid (91 g) at 90° C. The reaction was heated to 180–185° C. for 1 hour and was treated with water while hot. The mixture was stirred at 155° C. for 1 hour, heating was discontinued, and 3M HCl was added to the hot solution. The mixture was poured into water and filtered through diatomaceous earth. The filtrate was made basic with 15% aqueous sodium hydroxide, filtered thruogh diatomaceous earth, evaporated, and purified by chromatography (elluting with dichloromethane) to give 4-amino-2-bromobenzophenone (0.76 g) as a white solid; mp 157–160° C.; MS: m/z=276(M+1); NMR: 6.37 (s,2), 6.84 (d,1), 7.52 (m,3), 7.62 (m,3), 7.77 (m,1).Analysis for $C_{13}H_{10}BrNO$: Calculated: C, 56.73; H, 3.66; N, 5.09; Found: C, 56.21; H, 3.50; N, 5.00.

EXAMPLE 9

N-(4-Benzoyl-2-bromophenyl)-3,3,3,-trifluoro-2-hydroxy-2-methylpropanamide

To a stirred, cooled (−20° C.) solution of 3,3,3-trifluoro-2-hydroxy-2-methylpropanoic acid (0.75 g) in N,N-dimethylacetamide (10 mL) was rapidly added thionyl chloride (0.56 g) and the mixture stirred at −15 to −20° C. for 1 hour. 3-Bromo-4-aminobenzophenone (0.75 g) was then added in one portion and the mixture was allowed to stir at room temperature overnight. The solution was poured into ice water and the aqueous phase decanted from the resulting oily solid. Chromatography (eluent methylene chloride) gave the title compound (0.43 g) as a white solid; mp 138–40° C. Analysis for $C_{17}H_{13}BrF_3NO_3$: Calculated: C, 49.06; H, 3.15; N, 3.37; Found: C, 49.06; H, 3.10; N, 3.35.

EXAMPLE 10

N-(4-Benzoyl-2-cyanophenyl)-3,3,3,-trifluoro-2-hydroxy-2-methylpropanamide

To a stirred, cooled solution of 3,3,3-trifluoro-2-hydroxy-2-methylpropanoic acid (0.15 g) in methylene chloride (10 mL) was added thionyl chloride (0.12 g) and the mixture was stirred at reflux for 3 hours. The mixture was cooled to room temperature, triethylamine (0.11 g) added and the mixture stirred at reflux for 0.5 hour. The mixture was again cooled to room temperature, 3-cyano-4-aminobenzophenone (0.19 g) in tetrahydrofuran (2.5 mL) was added and the mixture stirred at reflux overnight. The solvent was evaporated and the residue partioned between ethyl acetate and 3N HCl. The organic layer was washed with water, dried and evaporated to yield a pale yellow oil. Chromatography (eluent methylene chloride then 2% ethyl ether in methylene chloride) gave the title compound (0.11 g) as a white solid; mp 202–204° C. Analysis for $C_{18}H_{13}F_3N_2O_b.0.5\ H_2O$: Calculated: C, 58.22; H, 3.80; N, 7,54; Found: C, 58.03; H, 3.57; N, 7.26.

The starting 3-cyano-4-aminobenzophenone was prepared as follows.

a. 3-Cyano-4-nitrobenzophenone. A stirred mixture of 3-chloro-4-nitrobenzophenone (5.00 g) and copper(I) cyanide (2.57 g) in dimethylformamide (50 mL) was heated at reflux for 16 hours. The hot reaction mixture was then poured into a stirred solution of ferric chloride (15.30 g) concentrated HCl (5 mL) and water (200 mL). The mixture was heated at 65–70° C. for 30 minutes, cooled to room temperature treated with ethyl acetate (250 mL) and stirred vigorously for 5 minutes. The organic phase was separated and the aqueous layer extracted with another 250 mL portion of ethyl acetate. The combined organics were dried, filtered and evaporated to give a brown oil. Chromatography (eluent toluene) gave 3-cyano-4-nitrobenzophenone (2.77 g) as a yellow solid; 117–119° C. Analysis for $C_{14}H_8N_2O_3$: Calculated: C, 66.67; H, 3.20; N, 11.11; Found: C, 66.83; H, 2.99; N, 11.12.

b. 3-Cyano-4-aminobenzophenone. To a stirred refluxing mixture of 3-cyano-4-nitrobenzophenone (1.50 g) and iron powder (3.64 g) in ethanol (50 mL) was added dropwise over 0.5 hour a solution of concentrate hydrochloric acid (0.35 mL) in ethanol (14 mL) and reflux was maintained overnight. The hot mixture was filtered through diatomaceous earth and the reaction flask and diatomaceous earth pad was washed with three 50 mL portions of ethanol. The combined filtrate was evaporated to yield a tan solid. Chromatography (eluent 10% to 40% ethyl acetate gradient in methylene chloride) gave 3-cyano-4-aminobenzophenone (0.21 g) as a tan solid; mp 158–160° C. Analysis for $C_{14}H_{10}N_2O.0.25\ H_2O$: Calculated: C, 74.35; H, 4.33; N, 12.32; Found: C, 74.16; H, 4.66; N, 12.35.

EXAMPLE 11

N-(4-Benzoyl-2-methoxyphenyl)-3,3,3,-trifluoro-2-hydroxy-2-methylpropanamide

To a stirred, cooled (−20° C.) solution of 3,3,3-trifluoro-2-hydroxy-2-methylpropanoic acid (0.52 g) in N,N-dimethylacetamide (5 mL) was rapidly added thionyl chloride (0.39 g) and the mixture stirred at −10 to −20° C. for 1 hour. 3-Methoxy-4-aminobenzophenone (0.50 g) was then added in one portion and the mixture allowed to stir at room temperature overnight. The solution was poured into water and the aqueous phase decanted from the resulting oily solid. Chromatography (eluent methylene chloride then 2% ethyl ether in methylene chloride) gave the title compound (0.37 g) as an off-white solid; mp 126–128° C. Analysis for $C_{18}H_{16}F_3NO_4.0.25\ H_2O$: Calculated: C, 58.14; H, 4.47; N, 3.77; Found: C, 58.29; H, 4.48; N, 3.78.

EXAMPLE 12

N-(4-Benzoyl-2-hydroxyphenyl)-3,3,3,-trifluoro-2-hydroxy-2-methylpropanamide

To a stirred, cooled (−20° C.) solution of 3,3,3-trifluoro-2-hydroxy-2-methylpropanoic acid (1.11 g) in N,N- dimethylacetamide (15 mL) was rapidly added thionyl chloride (0.84 g) and the mixture stirred at −10 to −20° C. for 1 hour. 3-Hydroxy-4-aminobenzophenone (1.00 g) was then added in one portion and the mixture allowed to stir at room temperature overnight. The solution was poured into ice water and the aqueous phase decanted from the resulting oily precipitate. Chromatography (eluent 2% to 5% methanol gradient in methylene chloride) yielded a white foam which was dissolved in a small amount of methylene chloride and added dropwise to stirred hexane (100 mL) to yield the title compound (0.86 g) as an white solid; mp 119–121° C. Analysis for $C_{17}H_{14}F_3NO_4$: Calculated: C, 57.79; H, 3.99; N, 3.96: Found: C, 57.85; H, 4.39; N, 3.72.

EXAMPLE 13

N-[2-Hydroxy-4-(4-pyridylsulfonyl)phenyl]-3,3,3,-trifluoro-2-hydroxy-2-methylpropanamide To a stirred suspension of N-[2-methoxy-4-(4-pyridylsulfonyl)phenyl]-3,3,3,-trifluoro-2-hydroxy-2-methyl propanamide (1.30 g) and sieve dried methylene chloride (50 mL) was added boron tribromide (1.6 mL of a 1.0 M solution in methylene chloride), and the mixture (a gummy ball of material and solvent) was stirred at reflux for 2 hours and then stirred overnight at room temperature. The reaction mixture was poured into water, made basic with saturated sodium bicarbonate solution and extracted with methylene chloride (2×250 mL; discarded) followed by ethyl acetate (100 mL). The ethyl acetate solution was dried, filtered, evaporated to a brown oil and purified by chromatography twice (eluent ethyl acetate and eluent methylene chloride-ethyl acetate (1:4)) to yield the title compound (0.15 g); mp 218–220° C. Analysis for $C_{15}H_{13}F_3N_2O_5S$: Calculated: C, 46.16; H, 3.36; N, 7.18: Found: C, 45.87; H, 3.47; N, 6.91.

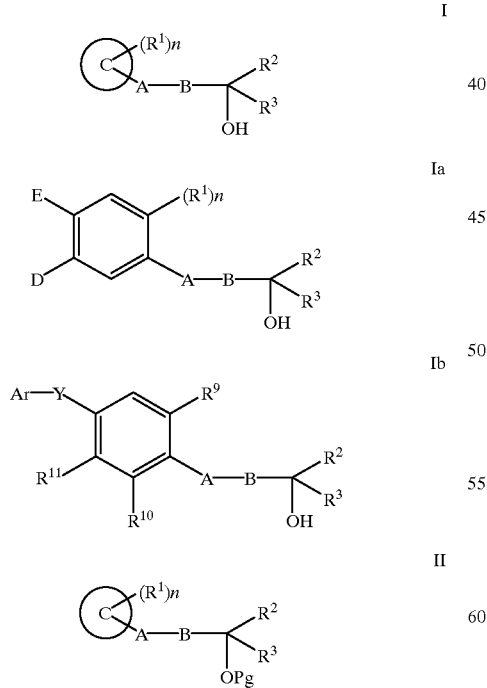

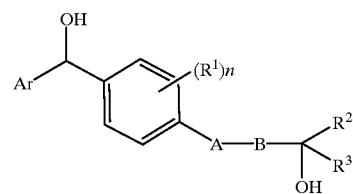

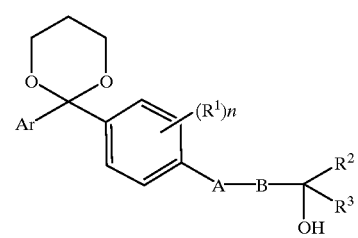

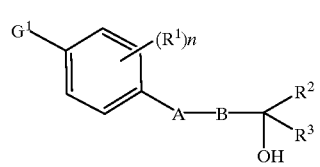

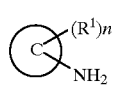

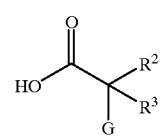

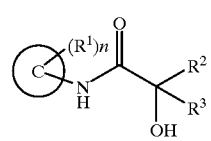

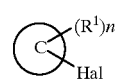

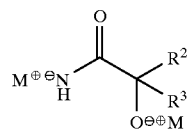

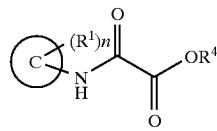

XII 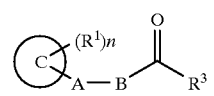

XIII 

XIV 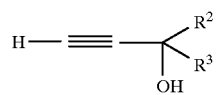

XV 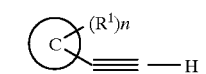

XVI 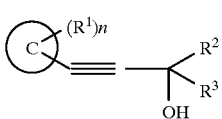

XVII 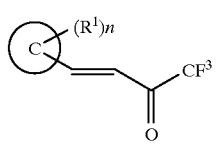

XVIII 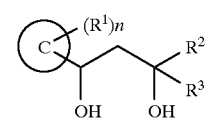

XIX 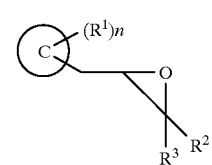

XX 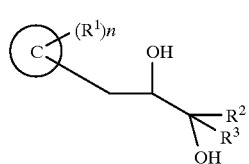

XXI 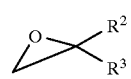

XXII 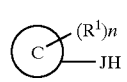

XXIII 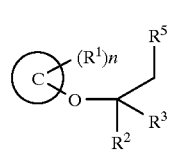

XXIV 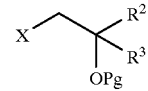

XXV 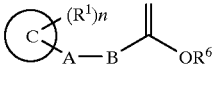

XXVI 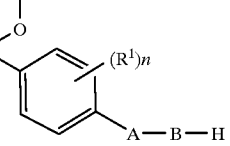

XXVII 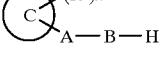

XXVIII 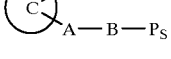

XXIX 

What is claimed is:

1. A compound of Formula Ib:

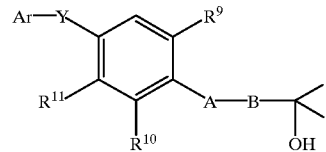

(Ib)

wherein $R^9$ is (1–4C)alkyl; $R^{10}$ is hydrogen; $R^{11}$ is hydrogen, halo, cyano, methoxy, hydroxy or methyl;

$R^2$ and $R^3$ are independently (1–3C)alkyl substituted by from 0 to 2k+1 atoms selected from fluoro and chloro wherein k is the number of carbon atoms in the said (1–3C)alkyl, provided that $R^2$ and $R^3$ are not both methyl; or $R^2$ and $R^3$, together with the carbon atom to which they are attached, form a 3–5 membered cycloalkyl ring optionally substituted by from 0 to 2m–2 fluorine atoms wherein m is the number of carbon atoms in said ring;

Ar is phenyl, wherein said phenyl may be substituted at carbon, with 0–4 substituents selected from (1–4C)alkyl, (1–4C)haloalkyl, (1–4C)alkoxy, (1–4C)haloalkoxy, (2–4C)alkenyloxy, cyano, nitro, halo and trifluoromethylthio;

Y is selected from carbonyl, sulfinyl and sulfonyl;

A—B is NHCO;

or a pharmaceutically acceptable in vivo hydrolyzable ester of said compound of formula Ib;

or a pharmaceutically acceptable salt of said compound or said ester.

2. A compound as claimed in claim 1, wherein Ar is phenyl; Y is sulfonyl; A—B is NHCO, $R^9$ is methyl; and $R^{10}$ and $R^{11}$ are hydrogen; Ar is phenyl; Y is carbonyl; A—B is NHCO; $R^9$ is methyl; and $R^{10}$ and $R^{11}$ are hydrogen.

3. A compound as claimed in claim 2 wherein said compound is N-(4-benzoyl-2-methylphenyl)-3,3,3-trifluoro-2-hydroxy-2-methylpropanamide, or (S)-(−)-N-(4-benzoyl-2-methylphenyl)-3,3,3-trifluoro-2-hydroxy-2-methylpropanamide.

4. A pharmaceutical composition comprising a compound of claim 1 or a pharmaceutically acceptable in vivo hydrolyzable ester of said compound of claim 1, or a pharmaceutically acceptable salt of said compound of claim 1 or said ester, and a pharmaceutically acceptable carrier or diluent.

5. A method of tracking urinary incontinence comprising administering to a mammal in need of such treatment an effective amount of a compound of claim 1.

6. A method of relaxing bladder smooth muscle comprising administering to a mammal in need of such treatment an effective amount of a compound of claim 1.

7. A method of treating asthma comprising administering to a mammal in need of such treatment an effective amount of a compound of claim 1.

* * * * *